US012465812B2

(12) United States Patent
Tseng et al.

(10) Patent No.: US 12,465,812 B2
(45) Date of Patent: Nov. 11, 2025

(54) DEVICE FOR PULMONARY REHABILITATION

(71) Applicants: TAIPEI MEDICAL UNIVERSITY, Taipei (TW); Shih-Fan Chen, La Canada Flt, CA (US)

(72) Inventors: Chien-Hua Tseng, Taipei (TW); Chien-Ling Su, Taipei (TW)

(73) Assignees: TAIPEI MEDICAL UNIVERSITY, Taipei (TW); Shih-Fan Chen, La Canada Flt, CA (US)

( * ) Notice: Subject to any disclaimer, the term of this patent is extended or adjusted under 35 U.S.C. 154(b) by 336 days.

(21) Appl. No.: 18/028,752

(22) PCT Filed: Sep. 28, 2021

(86) PCT No.: PCT/US2021/052275
§ 371 (c)(1),
(2) Date: Mar. 27, 2023

(87) PCT Pub. No.: WO2022/067220
PCT Pub. Date: Mar. 31, 2022

(65) Prior Publication Data

US 2023/0330484 A1 Oct. 19, 2023

Related U.S. Application Data

(60) Provisional application No. 63/171,591, filed on Apr. 7, 2021, provisional application No. 63/084,039, filed on Sep. 28, 2020.

(51) Int. Cl.
*A63B 23/18* (2006.01)
*A61M 16/00* (2006.01)
(Continued)

(52) U.S. Cl.
CPC ......... *A63B 23/18* (2013.01); *A61M 16/0006* (2014.02); *A61M 16/208* (2013.01);
(Continued)

(58) Field of Classification Search
CPC ................ A63B 23/18; A63B 24/0062; A63B 2220/833; A63B 21/0088; A63B 24/0087;
(Continued)

(56) References Cited

U.S. PATENT DOCUMENTS 3,674,910 A * 7/1972 McKenzie ............... G10D 7/14 984/137
4,196,650 A * 4/1980 Fricke .................. G10H 1/0558 84/718
5,042,467 A * 8/1991 Foley ................ A61M 15/0086 128/200.14
5,899,832 A * 5/1999 Hougen ................. A63B 23/18 482/13

(Continued)

FOREIGN PATENT DOCUMENTS

CN 211328018 U 8/2020
WO 2018/217707 A1 11/2018
WO 2020/058354 A1 3/2020

*Primary Examiner* — Garrett K Atkinson
(74) *Attorney, Agent, or Firm* — Winston Hsu

(57) ABSTRACT

Provided is a device for pulmonary rehabilitation. The device is configured to provide adjustable resistance for a patient during respiratory training on demands so as to improve rehabilitation efficiency. Moreover, the device is configured to adapt a variety of external parts to assist in medication dosing, information processing, and/or sputum removal for the patient during respiratory training. Therefore, optimal efficiency for pulmonary rehabilitation and smooth experience during respiratory training for the patient can be achieved.

20 Claims, 17 Drawing Sheets

(51) Int. Cl.
*A61M 16/20* (2006.01)
*A63B 24/00* (2006.01)

(52) U.S. Cl.
CPC . *A63B 24/0062* (2013.01); *A61M 2016/0027* (2013.01); *A61M 2205/3592* (2013.01); *A61M 2206/14* (2013.01); *A61M 2230/04* (2013.01); *A63B 2220/833* (2013.01)

(58) Field of Classification Search
CPC .... A63B 2024/0093; A63B 2071/0627; A63B 2071/065; A63B 2220/56; A63B 2225/50; A63B 2230/045; A63B 2230/40; A63B 21/00069; A63B 21/00196; A63B 23/032; A63B 71/0622; A61M 16/0006; A61M 16/208; A61M 2016/0027; A61M 2205/3592; A61M 2206/14; A61M 2230/04; A61M 15/0086; A61M 15/002; A61M 15/009; A61M 16/0866; A61M 2205/587; A61B 5/02; A61B 5/024; A61B 5/1455; A61B 5/0205; A61B 5/087
See application file for complete search history.

(56) References Cited

U.S. PATENT DOCUMENTS

| | | | | |
|---|---|---|---|---|
| 6,058,932 | A * | 5/2000 | Hughes | A61M 16/0006 482/13 |
| 6,083,141 | A * | 7/2000 | Hougen | A61M 16/0006 128/202.16 |
| 6,176,235 | B1 * | 1/2001 | Benarrouch | A61M 16/20 128/205.12 |
| 6,326,532 | B1 * | 12/2001 | Antaki | G10D 7/14 84/377 |
| 2006/0223675 | A1 * | 10/2006 | Lew | A63D 3/00 482/13 |
| 2013/0036893 | A1 * | 2/2013 | Schaman | G10D 7/14 84/377 |
| 2014/0174435 | A1 * | 6/2014 | Addington | A61M 11/06 128/200.21 |
| 2017/0157461 | A1 * | 6/2017 | Lyapko | A63B 23/18 |
| 2017/0189629 | A1 * | 7/2017 | Newberry | A61B 5/087 |
| 2018/0330702 | A1 * | 11/2018 | Schille | G10H 1/386 |

* cited by examiner

DEVICE FOR PULMONARY REHABILITATION

TECHNICAL FIELD

The present disclosure relates to a respiratory therapy, and more particular to a device for pulmonary rehabilitation.

DESCRIPTION OF RELATED ART

With the exacerbation of population ageing and air pollution stemming from industrial developments, the prevalence rate of chronic obstructive pulmonary disease (COPD) worldwide is rising each year, impacting more than 10 to 20% of the population of the majority of the world's developed countries. Chronic respiratory diseases such as pulmonary obstruction, pulmonary aging, asthma, or bronchiectasis mostly lead to bronchial collapse at a later phase of the respiratory cycle, which further results in air trapping in the lungs and hinders the removal of carbon dioxide therefrom. In addition, patients with COPD often suffer from breathing difficulty during exercise since forced expiration amplifies their respiratory tract collapse. However, the current means of medical treatment for the above situation lacks in solutions to ensure respiratory tract of a patient to stay unobstructed, free (reduced) of sputum, or enhance its gas exchange mechanism during expiratory, much less to help enhance the patient's physical ability through rehabilitation.

Current clinical treatments for the patients described above is focused on rehabilitation through inhaled medication or oral medication, while physical interventions, which are simple and effective, are easily neglected by most clinicians. For example, an exhalation trainer allows a patient to push away a spring disposed therein, which provides a fixed exhale resistance, through exhalation, so as to improve respiratory performance of the patient. However, exhale resistance of existing exhalation trainers typically cannot be adjusted in response to user's exhalation conditions that may thus result in insufficient or overwhelming exhale resistance or an unsmooth expiration process for the patient.

Therefore, there is still an unmet need in the art to develop a device for pulmonary rehabilitation to solve the above problems.

SUMMARY

In view of the foregoing, the present disclosure provides a device for pulmonary rehabilitation, comprising: a respiratory adjustment unit having a first opening end and a second opening end, wherein the first opening end is in communication with the second opening end to form a first flow channel, and wherein the respiratory adjustment unit further comprises a first adjustment gate disposed in the first flow channel and having a first aperture with an adjustable size.

In at least one embodiment of the present disclosure, the respiratory adjustment unit has a third opening end in communication with the first opening end to form a second flow channel, wherein the respiratory adjustment unit further comprises a second adjustment gate disposed in the second flow channel and having a second aperture with an adjustable size.

In at least one embodiment of the present disclosure, the first adjustment gate comprises a first baffle having the first aperture disposed thereon and a first blade configured to slide on the first baffle to partially or completely cover the first aperture, or the second adjustment gate comprises a second baffle having the second aperture disposed thereon and a second blade configured to slide on the second baffle to partially or completely cover the second aperture.

In at least one embodiment of the present disclosure, the first baffle has a first sliding slot, and the first blade has a first surface with a first pillar and a second surface opposed to the first surface, wherein the first pillar is disposed in the first sliding slot and configured to reciprocate along a long axial direction of the first sliding slot; and the second baffle has a third sliding slot, and the second blade has a third surface with a third pillar and a fourth surface opposed to the third surface, wherein the third pillar is disposed in the third sliding slot and configured to reciprocate along a long axial direction of the third sliding slot.

In at least one embodiment of the present disclosure, the first adjustment gate further comprises a first rotation part having a second sliding slot, the second surface of the first blade has a second pillar disposed in the second sliding slot and configured to reciprocate along a long axial direction of the second sliding slot, and the first rotation part is configured to drive the first pillar and the second pillar to reciprocate within the first sliding slot and the second sliding slot respectively during a rotation state of the first rotation part, thereby enabling the first blade to slide on the first baffle; and the second adjustment gate further comprises a second rotation part having a fourth sliding slot, the fourth surface of the second blade has a fourth pillar disposed in the fourth sliding slot and configured to reciprocate along a long axial direction of the fourth sliding slot, and the second rotation part is configured to drive the third pillar and the fourth pillar to reciprocate within the third sliding slot and the fourth sliding slot respectively during a rotation state of the second rotation part, thereby enabling the second blade to slide on the second baffle.

In at least one embodiment of the present disclosure, the first adjustment gate comprises: a first baffle having a plurality of first perforations with different sizes; and a first rotation part covering the first baffle and having a first through hole formed thereon, wherein the first rotation part is configured to rotate with respect to the first baffle, thereby enabling the first through hole to expose at least one of the plurality of first perforations with different sizes to form the first aperture; or the second adjustment gate comprises: a second baffle having a plurality of second perforations with different sizes; and a second rotation part covering the first baffle and having a second through hole formed thereon, wherein the second rotation part is configured to rotate with respect to the second baffle, thereby enabling the second through hole to expose at least one of the plurality of second perforations with different sizes to form the second aperture.

In at least one embodiment, the device of the present disclosure further comprises a combination of a first pressure sensor and a second pressure sensor or a combination of a third pressure sensor and a fourth pressure sensor, wherein the first pressure sensor is disposed in the first flow channel at one side of the first adjustment gate to measure a first pressure signal; the second pressure sensor is disposed in the first flow channel at another side of the first adjustment gate to measure a second pressure signal; the third pressure sensor is disposed in the second flow channel at one side of the second adjustment gate to measure a third pressure signal; and the fourth pressure sensor is disposed in the second flow channel at another side of the second adjustment gate to measure a fourth pressure signal.

In at least one embodiment, the device of the present disclosure further comprises a processing module coupled with the combination of the first pressure sensor and the second pressure sensor to receive and process the first pressure signal and the second pressure signal, or coupled with the combination of the third pressure sensor and the fourth pressure sensor to receive and process the third pressure signal and the fourth pressure signal.

In at least one embodiment of the present disclosure, a distance between the first pressure sensor and the first adjustment gate is shorter than a distance between the first pressure sensor and the first opening end, and a distance between the third pressure sensor and the second adjustment gate is shorter than a distance between the third pressure sensor and the first opening end.

In at least one embodiment of the present disclosure, the first pressure sensor is plural and arranged in an opposite manner on an inner wall of the first flow channel; the second pressure sensor is arranged on the inner wall of the first flow channel; the third pressure sensor is plural and arranged in an opposite manner on an inner wall of the second flow channel; and the fourth pressure sensor is arranged on the inner wall of the second flow channel.

In at least one embodiment, the device of the present disclosure further comprises: a first check valve disposed in the first flow channel to block airflow flowing from the second opening end to the first opening end; and a second check valve disposed in the second flow channel to block the airflow flowing from the third opening end to the first opening end.

In at least one embodiment, the device of the present disclosure further comprises a dosing unit coupled with the third opening end to provide medication into the second flow channel.

In at least one embodiment, the device of the present disclosure further comprises: a vibration generating unit coupled with the second opening end, the third opening end, the first flow channel, the second channel, or a combination of two or more thereof to induce vibration and thereby to resonate the first flow channel or the second flow channel.

In at least one embodiment, the device of the present disclosure further comprises a processing module, wherein the vibration generating unit comprises a vibration sensor configured to measure a vibration signal, and wherein the processing module is coupled with the vibration generating unit to receive and process the vibration signal.

In at least one embodiment of the present disclosure, the vibration generating unit has a fourth opening end and a fifth opening end, and the fourth opening end is in communication with the fifth opening end to form a third flow channel, and wherein a vibration element is disposed within the third flow channel, the fourth opening end is coupled with the second opening end, and the fifth opening end is detachably coupled with the third opening end.

In at least one embodiment, the device of the present disclosure further comprises: a cardiovascular sensor coupled with the respiratory adjustment unit and configured to measure a cardiovascular signal; and a processing module coupled with the cardiovascular sensor to receive and process the cardiovascular signal.

In at least one embodiment, the device of the present disclosure further comprises: an indicating device coupled with the processing module and configured to send indication information to a user based on an adjustment instruction sent by the processing module.

In at least one embodiment of the present disclosure, the processing module is coupled with the first adjustment gate to send an adjustment instruction to the first adjustment gate, and the first adjustment gate is configured to adjust the size of the first aperture based on the adjustment instruction, or the processing module is coupled with the second adjustment gate to send the adjustment instruction to the second adjustment gate, and the second adjustment gate is configured to adjust the size of the second aperture.

In at least one embodiment of the present disclosure, the adjustment instruction is generated according to the first pressure signal, the second pressure signal, the third pressure signal, the fourth pressure signal, or a combination of two or more thereof, provided that the processing module receives and processes the first pressure signal, the second pressure signal, the third pressure signal, the fourth pressure signal, or the combination of two or more thereof; the adjustment instruction is generated according to the vibration signal, provided that the processing module receives and processes the vibration signal; and the adjustment instruction is generated according to the cardiovascular signal, provided that the processing module receives and processes the cardiovascular signal.

In at least one embodiment, the device of the present disclosure further comprises: a wireless transmission module coupled with the processing module and configured to receive and send an outside signal to the processing module for generating the adjustment instruction or to send a signal received and processed by the processing module to the outside.

In summary, the device for pulmonary rehabilitation of this disclosure not only solves problems of prior art where exhalation trainer provides insufficient and non-adjustable exhale resistance, but also provides the following functionalities and effects in some embodiments:

I. an adjustable resistance device in an airflow channel: where physical properties are utilized for the patient to exhale through apertures of various diameters to form positive pressure derived from various resistance in the air flow channel generated by exhale forces for the bronchial of the patient to exhale smoothly;

II. a vibrating sputum disposal design: where a vibration generating mechanism is utilized to induce vibration to the air flow channel via flow variance in the patient's exhalation, thereby assisting the patient to cough out sputum;

III. synchronous training of lung and facial muscles: where a mouthpiece of the device for pulmonary rehabilitation of this disclosure is designed to correct mouth shape of the patient during exhalation, thereby providing orbicularis muscle training to improve pulmonary rehabilitation efficiency;

IV. visual feedback: where a visualized instruction is feedback to the patient to assist in adjusting optimized exhalation force, thereby facilitating the patient to effectively remove lingering gas in the lungs; and V. sensing and warning mechanism: where sensing mechanisms are provided to detect and record respiratory performance of the patient, thereby determining the optimal adjustment to exhalation force for the patient and detecting deterioration of respiratory tracts at an early stage.

DETAILED DESCRIPTION OF THE EMBODIMENTS

The following embodiments are provided to illustrate the present disclosure in detail. A person having ordinary skill in the art can easily understand the advantages and effects of the present disclosure after reading the disclosure of this specification, and also can implement or apply in other different embodiments. Therefore, it is possible to modify and/or alter the following embodiments for carrying out this disclosure without contravening its scope for different aspects and applications, and any element or method within the scope of the present disclosure disclosed herein can combine with any other elements or methods disclosed in any embodiments of the present disclosure.

The proportional relationships, structures, sizes and other features shown in accompanying drawings of this disclosure are only used to illustrate embodiments describe herein, such that those with ordinary skill in the art can read and understand the present disclosure therefrom, of which are not intended to limit the scope of this disclosure. Any changes, modifications, or adjustments of said features, without affecting the designed purposes and effects of the present disclosure, should all fall within the scope of the technical content of this disclosure.

As used herein, when describing an object "comprises," "includes" or "has" a limitation, unless otherwise specified, it may additionally include other elements, components, structures, regions, parts, devices, systems, steps, connections, etc., and should not exclude other limitations.

As used herein, the terms such as "above," "under," "left," "right," "internal," "external," etc. are only cited in convenience of illustrating embodiments of this disclosure, which are not intended to limit the scope of this disclosure. Any adjustment, exchange, or alteration in relative positions and relationships, without substantially changing the technical content of this disclosure, should all fall within the scope of this disclosure.

As used herein, sequential terms such as "first," "second," etc. are only cited in convenience of describing or distinguishing limitations such as elements, components, structures, regions, parts, devices, systems, etc. from one another, which are not intended to limit the scope of this disclosure, nor to limit spatial sequences between such limitations. Further, unless otherwise specified, wordings in singular forms such as "a" and "the" used herein also pertain to plural forms, and wordings such as "or" and "and/or" may be used interchangeably.

As used herein, numeral ranges are inclusive and compatible. Any number falls within said numeral ranges may be taken as a maximum value or a minimum value for deriving sub-ranges therefrom. For example, a numeral range of "3 to 11 mm" should be understood as any sub-range between a minimum value of 3 mm to a maximum value of 11 mm, such as 3 mm to 5 mm, 7 mm to 11 mm, 3.5 mm to 4.5 mm, etc.

Figure 1:
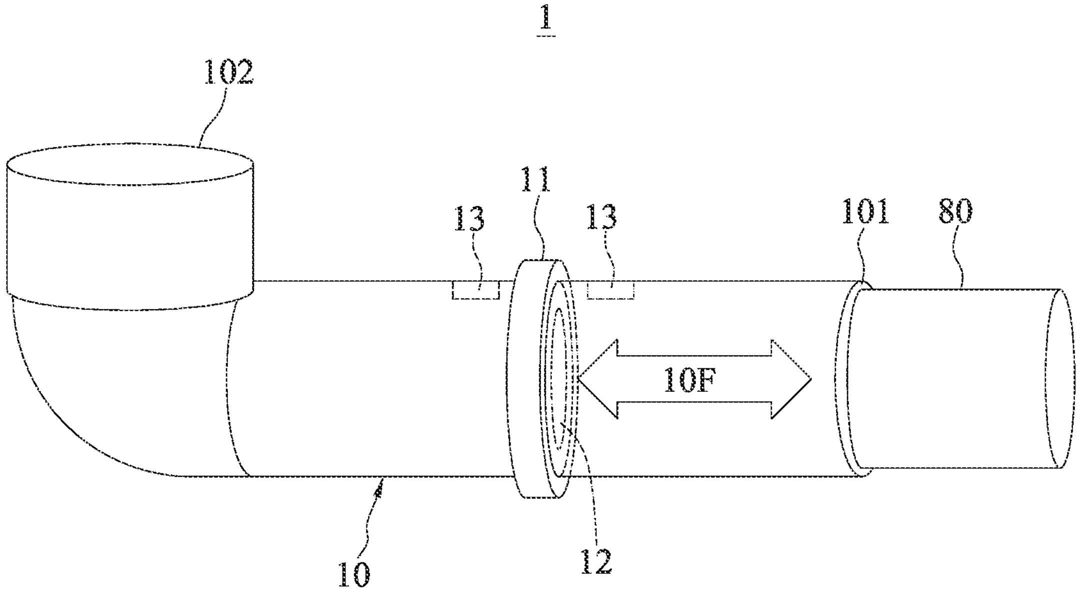
FIG. 1 is a schematic diagram illustrating an embodiment of the structure of a device for pulmonary rehabilitation in accordance with the present disclosure.

Referring to FIG. 1, a device 1 of the present application for pulmonary rehabilitation is disclosed. In at least one embodiment, the device 1 is mainly comprised of a respiratory adjustment unit 10 and a mouthpiece 80. For example, the respiratory adjustment unit 10 has a first opening end 101 and a second opening end 102 in communication with each other to form a flow channel 10F, and the mouthpiece 80 is coupled to the first opening end 101 to allow a patient to perform respiratory training therefrom.

Moreover, the respiratory adjustment unit 10 further comprises an adjustment gate 11 having an aperture 12 with an adjustable size, so as to control the amount of airflow through the aperture 12, thereby providing determined resistance in the flow channel 10F for the patient during respiratory training. A detailed description of the adjustment gate 11 will be discussed later in this disclosure.

In some embodiments, one or more pressure sensors 13 may be provided in the flow channel 10F, so as to monitor pressure signals related to the patient's respiratory performance. For example, said pressure sensors 13 may be used to detect positive pressure derived from resistance in the flow channel 10F generated by exhale/inhale forces of the patient, such that the respiratory performance of the patient may be determined and adjustment to the adjustment gate 11 may be optimized. A detailed description of the pressure sensors 13 will be discussed later in this disclosure.

In one embodiment, the mouthpiece 80 has a tubular shape for the patient to bite on, such that the patient may simultaneously train his/her orbicularis muscle during respiratory training by correcting his/her mouth into a pouting shape to allow smooth breathing via the device 1. However, the shape of the mouthpiece 80 may be varied based on design purposes, of which the present disclosure is not limited thereto.

In some embodiments, an external part may be detachably coupled to the device 1 (e.g., the second opening end 102 or other suitable regions of the device 1) to further assist the efficiency of the respiratory training. Said external part may be either a dosing unit 20, a vibration generating unit 30, a processing module 40, a cardiovascular sensor 50, an indicating device 60, a wireless transmission module 70, or any combination thereof.

In some embodiments, the dosing unit 20 is configured to provide medication into the flow channel 10F, thereby enabling the patient to inhale medication during respiratory training.

In some embodiments, the vibration generation unit 30 is configured to induce vibration and resonate the flow channel 10F, such that the vibration may assist the patient to cough out sputum during respiratory training. A detailed description of the vibration generation unit 30 will be discussed later in this disclosure.

In some embodiments, the processing module 40 is configured to process any signal derived from the respiratory training of the patient. For example, an artificial learning mechanism may be implemented in the processing module 40 to monitor the respiratory performance of the patient, thereby determining optimal adjustment to the size of the aperture 12 for the patient during respiratory training and detecting deterioration of respiratory tracts at early stages. A detailed description of the processing module 40 will be discussed later in this disclosure.

In some embodiments, the cardiovascular sensor 50 is configured to measure a cardiovascular signal such as a blood oxygen signal, a blood pressure signal, a heartrate signal or the like from the patient during respiratory training. Said cardiovascular signal can be useful for monitoring the respiratory performance of the patient. For example, a cardiovascular signal may be related to the force output by the patient during respiratory training, and thus may be used to determine optimal adjustment to the size of the aperture 12 for the patient during respiratory training and detect deterioration of respiratory tracts at early stages.

In some embodiments, the indicating device 60 is configured to provide indication information such as air pressure, airflow rate, airflow volume, respiratory frequency, airflow entropy, and the like to the patient (or a user) to remind of the respiratory performance of the patient during respiratory training. For example, said indication information may indicate that the patient is breathing too hard or too light through the device 1, such that necessary adjustment to the aperture 12 is needed to ensure rehabilitation efficiency. A detailed description of the indicating device 60 will be discussed later in this disclosure.

In some embodiments, the wireless transmission module 70 is configured to receive or transmit any signal related to the patient during respiratory training via a wireless means such as Wi-Fi, Bluetooth, ZigBee, radio, infrared, and the like. For example, signals regarding the patient's respiratory performance may be received by the wireless transmission module 70 before sending to the processing module 40 for processing, and any signals generated by the processing module 40 may be transmitted by the wireless transmission module 70 for further use (e.g., adjusting the size of the aperture 12, adjusting vibrate capability of the vibration generating unit 30, displaying indication information on the indicating device 60, etc.).

It should be understood that, even without the aforementioned external part(s) (i.e., the external parts are detachably coupled), the device 1 described in FIG. 1 would still possess adequate functionality for pulmonary rehabilitation for the patient.

Figure 2:
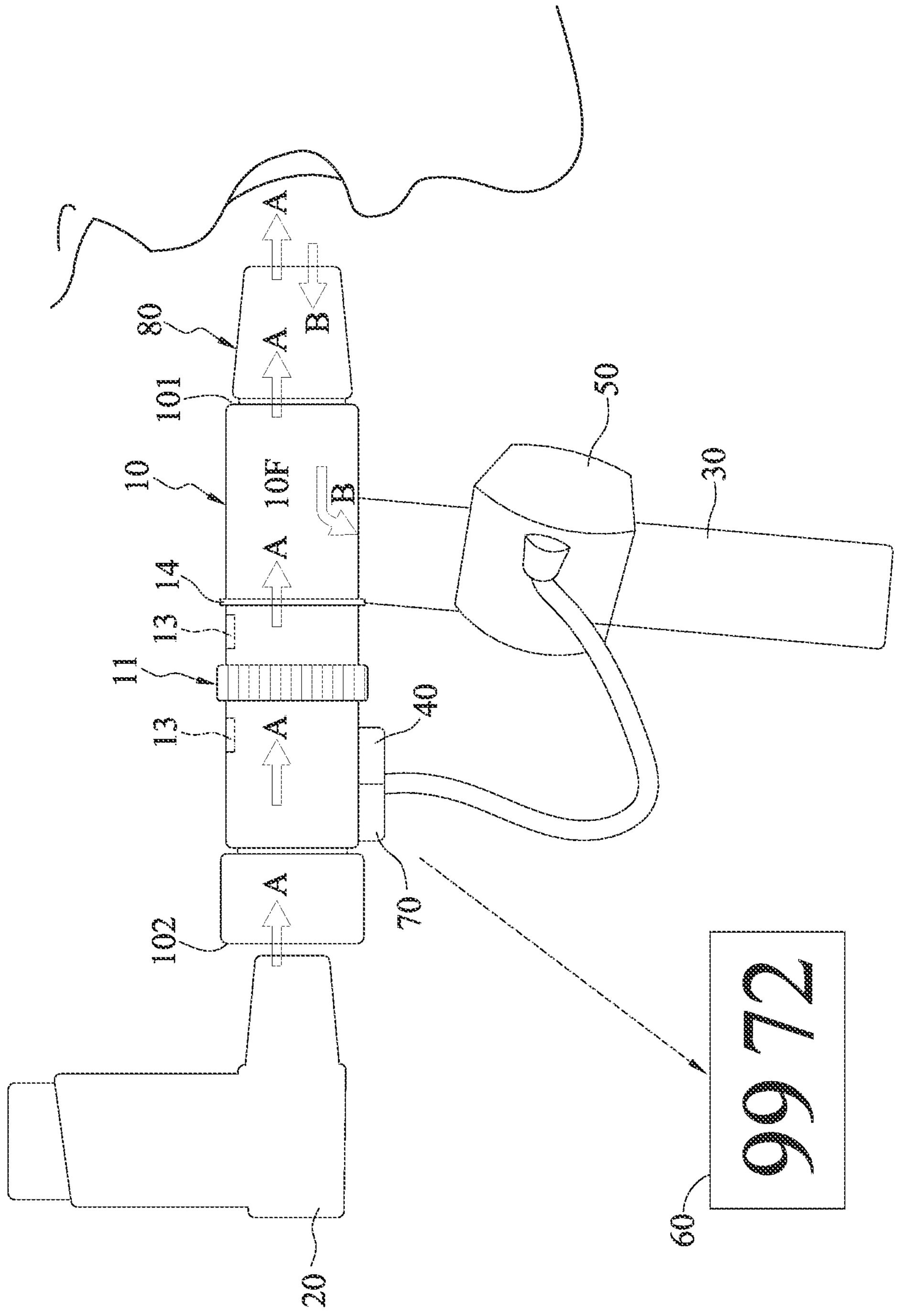
FIG. 2 is a schematic diagram illustrating an embodiment of the structure of a device for pulmonary rehabilitation in accordance with the present disclosure.

Referring to FIG. 2, a device 1 of the present application for pulmonary rehabilitation is disclosed. In at least one embodiment, the device 1 also comprises a respiratory adjustment unit 10 having a first opening end 101 where a mouthpiece 80 is coupled thereto, and a second opening end 102 in communication with the first opening end 101 to form a flow channel 10F. Similarly, the respiratory adjustment unit 10 further comprises an adjustment gate 11 having an aperture 12 with an adjustable size that provides determined resistance in the flow channel 10F for the patient during respiratory training, and one or more pressure sensors 13 for monitoring pressure signals related to the patient's respiratory performance.

In some embodiments, the respiratory adjustment unit 10 of the device 1 illustrated in FIG. 2 is configured to adapt at least a dosing unit 20 and a vibration generating unit 30 of the aforementioned external parts simultaneously. For example, the dosing unit 20 is coupled to the second opening end 102 of the respiratory adjustment unit 10, while the vibration generating unit 30 is coupled to the flow channel 10F at a location between the adjustment gate 11 and the first opening end 101. Further, a check valve 14 is also disposed in the flow channel 10F between the adjustment gate 11 and the coupling location to the vibration generating unit 30, so as to prevent air flow in a direction from the first opening end 101 to the second opening end 102. In this configuration, the check valve 14 will define a single-direction inhaling route and a single-direction exhaling route, respectively, for the patient during respiratory training, where the single-direction inhaling route (referring to the direction marked by arrows A) allows the patient to inhale medication through the flow channel 10F in a direction from the dosing unit 20 (if present), the second opening end 102, the adjustment gate 11, the check valve 14, the first opening end 101 and the mouthpiece 80 into the patient, and the single-direction exhaling route (referring to the direction marked by arrows B) allows the patient to exhale air through the flow channel 10F in a direction from the mouthpiece 80 through the first opening end 101 to the vibration generating unit 30 (if present). By distinguishing the inhale direction and the exhale direction in the device 1 for the patient, training efficiency is less likely to be affected by air lost in undesired direction (e.g., the check valve 14 may prevent air flow from the first opening end 101 to the second opening end 102 and/or the vibration generating unit 30 during inhale, or the check valve 14 may prevent air flow from the second opening end 102 and/or the vibration generating unit 30 to the first opening end 101 during exhale).

In addition to the configuration mentioned above, the device 1 of FIG. 2 may also adapt other external parts. For example, a cardiovascular sensor 50 may be attached to the device 1 (e.g., an outer surface of the vibration generating unit 30 where the patient is holding) to measure a cardiovascular signal from the patient. In some embodiments, a wireless transmission module 70 may be attached to the respiratory adjustment unit 10 to receive or transmit any signal related to the patient during respiratory training. In some embodiments, a processing module 40 may be attached to or wirelessly connected (e.g., via the wireless transmission module 70) to the respiratory adjustment unit 10 to process any signal derived from the respiratory training of the patient. In some embodiments, an indicating device 60 may be attached to or wirelessly connected (e.g., via the wireless transmission module 70) to the respiratory adjustment unit 10 to provide indication information to the patient (or a user) regarding the respiratory performance of the patient during respiratory training.

It should be understood that the configuration of the device 1 of the present application is not limited to those described above, and the elements shown in FIG. 2 can be altered based on design needs. For example, the coupling location of the dosing unit 20 and the vibration generating unit 30 may be switched (that is, reverse direction of arrows A will be known as the exhaling route and reverse direction of arrows B will be known as the inhaling route), and any aforementioned external parts may be eliminated, additionally attached to or relocated in other arrangements, of which the present disclosure is not limited thereto.

It should further be understood that, even without the aforementioned external parts (i.e., the external parts are detachably coupled), the device 1 described in FIG. 2 would still possess adequate functionality for pulmonary rehabilitation for the patient.

Figure 3A:
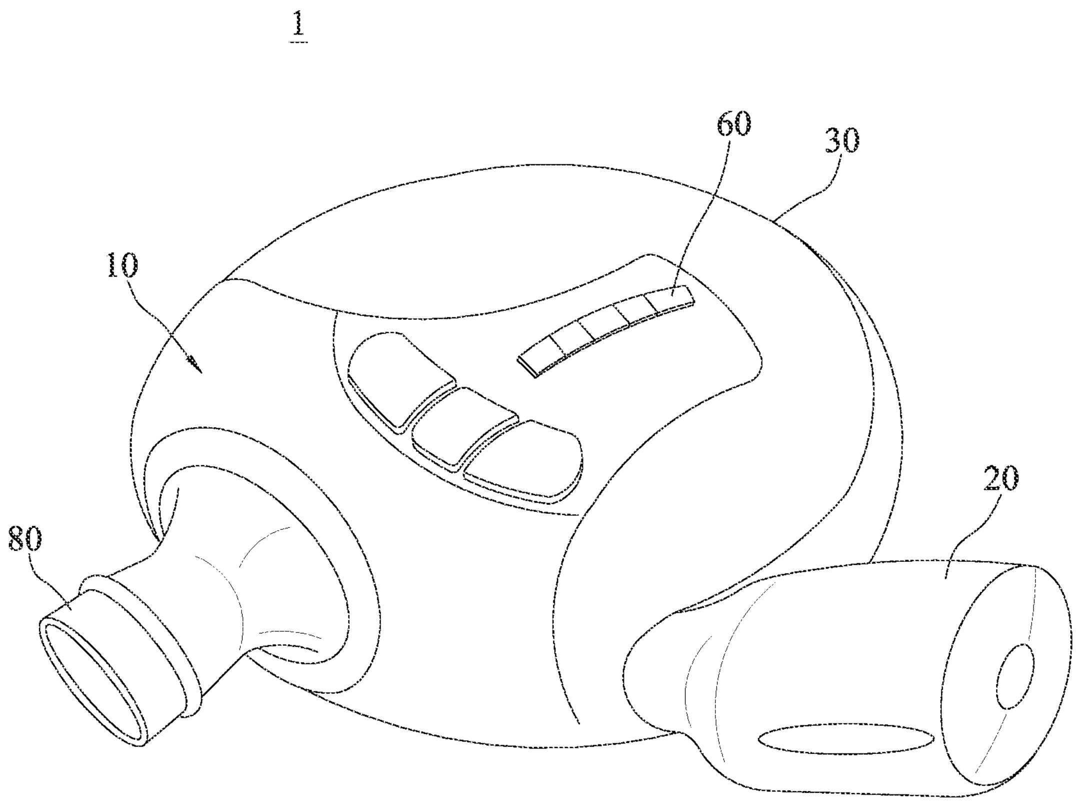
FIG. 3A is a schematic diagram illustrating an embodiment of the structure of a device for pulmonary rehabilitation in accordance with the present disclosure.
Figure 3B:
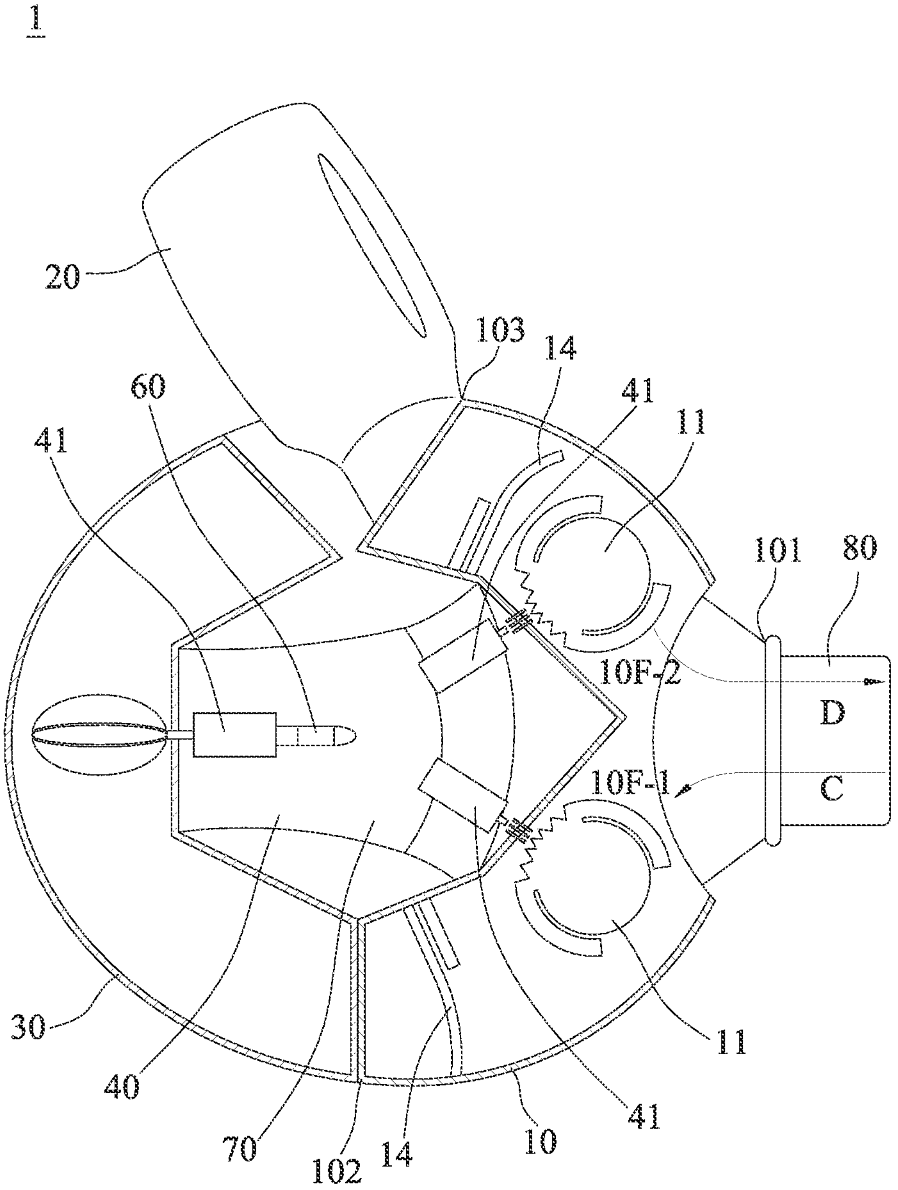
FIG. 3B is a schematic cross-sectional view of the structure of FIG. 3A.

Referring to FIGS. 3A and 3B, a device 1 of the present application for pulmonary rehabilitation is disclosed. In at least one embodiment, the respiratory adjustment unit 10 is designed in a "Y" shape to further distinguish the inhale direction and the exhale direction for the patient during respiratory training. In some embodiments, the shape of the respiratory adjustment unit 10 is not limited to the "Y" shape, and the angle between the flow channels thereof can be adjusted according to actual needs; for example, the respiratory adjustment unit 10 may be designed in a "T" shape.

In some embodiments, the respiratory adjustment unit 10 shown in FIGS. 3A and 3B comprises a first opening end 101 where a mouthpiece 80 is coupled thereto, a second opening end 102 in communication with the first opening end 101 to form a first flow channel 10F-1, and a third opening end 103 in communication with the first opening end 101 to form a second flow channel 10F-2. In this scenario, the first flow channel 10F-1 will define a single-direction exhaling route (referring to the direction marked by arrow C), and the second flow channel 10F-2 will define a single-direction inhaling route (referring to the direction marked by arrow D). Each of the first and second flow channels 10F-1 and 10F-2 has an adjustment gate 11 having an aperture 12 with an adjustable size disposed therein to provide determined resistance for said exhaling route and/or inhaling route.

In some embodiments, there may be one or more pressure sensors 13 provided in the first and second flow channels 10F-1 and 10F-2 about the adjustment gates 11, so as to monitor pressure signals related to the patient's respiratory performance. Further, check valves 14 may be disposed in each of the first and second flow channels 10F-1 and 10F-2, so as to ensure air flow in desired direction (e.g., the directions indicated by arrows C and D) for said exhaling and inhaling routes.

In at least one embodiment, as shown in FIGS. 3A and 3B, the respiratory adjustment unit 10 of the device 1 is configured to detachably coupled with external part(s).

In some embodiments, the vibration generating unit 30 may be coupled with the second opening end 102 and/or the third opening end 103 to induce vibration and resonate the first flow channel 10F-1 and/or the second flow channel 10F-2. In some embodiments, the first and second flow channels 10F-1 and 10F-2 may be connected into a circular channel. Therefore, the vibration generating unit 30 (if present) may induce vibration into the exhaling route or inhaling route during respiratory training of the patient.

In some embodiments, the second flow channel 10F-2 is configured to be coupled with the dosing unit 20 (e.g., allowing the dosing unit 20 to be inserted to the third opening end 103 via direct attachment or a connecting part). In some embodiments, the connecting part may be made of rubber that can adapt to different shapes of the dosing unit 20. In some embodiments, the dosing unit 20 may provide medication only into the inhaling route (e.g., the direction indicated by arrow D) during respiration of the patient due to the directional action of the check valves 14 as mentioned above. In some embodiments, one or more pressure sensors 13 disposed in the first and second flow channels 10F-1 and 10F-2 about the adjustment gates 11 are configured to monitor the flow rate to prevent the patient from inhaling the medicine too quickly.

In at least one embodiment, the respiratory adjustment unit 10 of the device 1 may be used alone for the patient to achieve optimal respiratory training efficiency without the vibration generating unit 30 and the dosing unit 20. In some embodiments, one or more pressure sensors 13 disposed in the first and second flow channels 10F-1 and 10F-2 about the adjustment gates 11 are configured to monitor whether the patient's breathing rate meets the training program (e.g., inhalation for 2 seconds and exhalation for 5 seconds) indicated by the doctor.

Further, as shown in FIGS. 3A and 3B, other external parts may also be present. For example, a processing module 40, an indicating device 60, and a wireless transmission module 70 may be disposed at a confluence of the first and second flow channels 10F-1 and 10F-2 of the respiratory adjustment unit 10 (e.g., the middle of the "Y" shape), so as to receive, process, transmit, or indicate signals related to the patient's respiratory performance. Moreover, one or more motors 41 may be disposed in said confluence and connected to the adjustment gates 11 and/or the vibration generating unit 30, respectively, so as to automatically adjust sizes of apertures 12 on the adjustment gates 11 or start/stop the vibration generating unit 30 based on adjustment instructions produced by the processing module 40.

It should be understood that the configuration of the device 1 of the present application is not limited to those described above, and the elements shown in FIGS. 3A and 3B can be altered based on actual needs. For example, any aforementioned external parts may be eliminated, additionally attached to or relocated in other arrangements, of which the present disclosure is not limited thereto.

It should be further understood that, even without the aforementioned external parts (i.e., the external parts are detachably coupled), the device 1 described in FIGS. 3A and 3B would still possess adequate functionality for pulmonary rehabilitation for the patient.

FIGS. 4 to 9 detail variations of the adjustment gate 11 and its relationship with other components in the device 1 in accordance with embodiments of the present disclosure.

Figure 4:
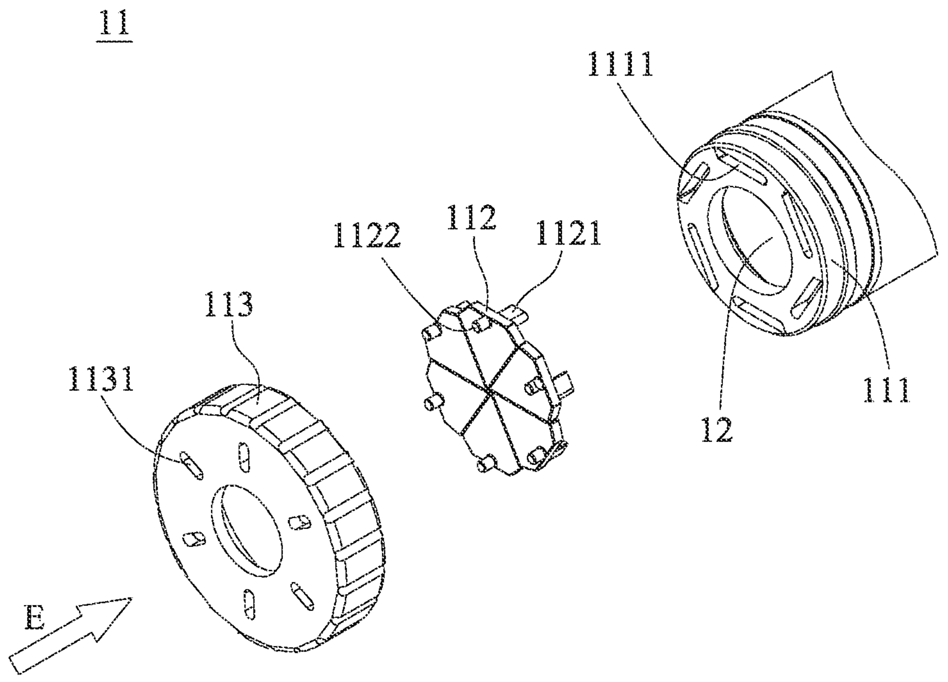
FIG. 4 is a schematic diagram illustrating an embodiment of the structure of an adjustment gate in accordance with the present disclosure.

Referring to FIG. 4, an adjustment gate 11 of the present application is disclosed. In at least one embodiment, the adjustment gate 11 comprises a baffle 111 having the aperture 12 disposed thereon, one or more blades 112 configured to slide on the baffle 111 to partially or completely cover the aperture 12 (i.e., the aperture 12 has an adjustable size), and a rotation part 113 that enables the baffle 111 and the one or more blades 112 to perform adjustment to the aperture 12 during a rotation state.

Each of the blade 112 has a first surface facing the baffle 111 and a second surface opposed to the first surface and facing the rotation part 113. The first surface has a pillar 1121 that is disposed in a corresponding sliding slot 1111 (arranged in regular polygon and corresponding in number of the blades 112) of the baffle 111. The second surface also has a pillar 1122 that is disposed in a corresponding sliding slot 1131 (arranged in radial and corresponding in number of the blades 112) of the rotation part 113. In such configuration, as the rotation part 113 rotates, the pillars 1121 and 1122 will be driven to reciprocate along a long axial direction of the respective sliding slots 1111 and 1131, in turn driving the blades 112 to slide on the baffle 111 (the baffle 111 is fixed inside the flow channel 10F) to adjust coverage on the aperture 12 (i.e., adjust the size of the aperture 12). Accordingly, resistance in the flow channel 10F will be determined by coverage of the aperture 12 for the patient to achieve optimal respiratory training efficiency.

Figure 5A:
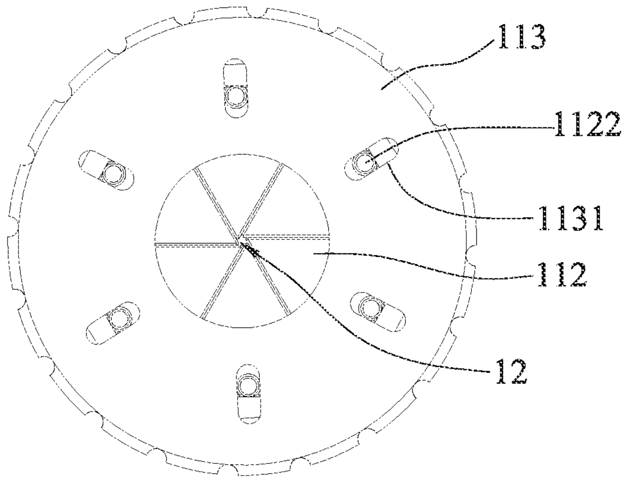
FIGS. 5A and 5B are schematic diagrams illustrating the adjustment gate of FIG. 4 in a static state.
Figure 5B:
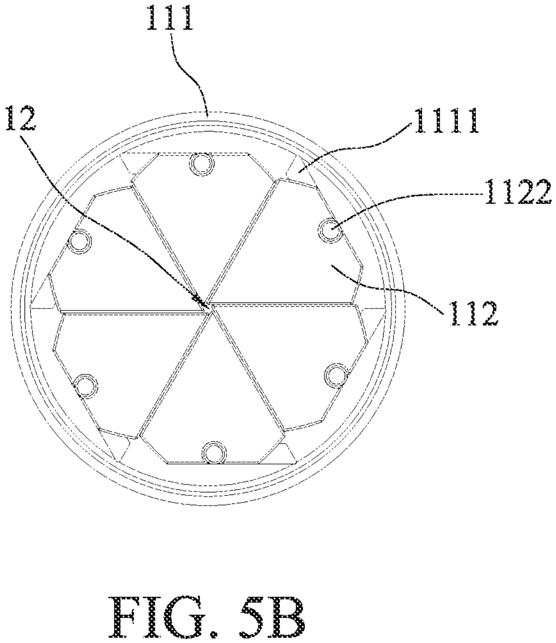

FIGS. 5A and 5B illustrate a state observed from the direction of arrow E shown in FIG. 4, where the aperture 12 is set in its minimum diameter (completely covered by the blades 112 or having an extremely small passage) using an adjustment gate 11 of the present disclosure. For example, FIG. 5A shows that the pillars 1122 of the blades 112 are respectively moved to one ends of the sliding slots 1131 (along their long axial direction) that are closest to the center of the aperture 12, while FIG. 5B shows that with the blades 112 closing up the aperture 12, one ends of the sliding slots 1111 that are away from the center of the aperture 12 are exposed by the blades 112, indicating that the pillars 1121 have been respectively moved to another ends of the sliding slots 1111 (along their long axial direction) that are closest to the center of the aperture 12.

Figure 6A:
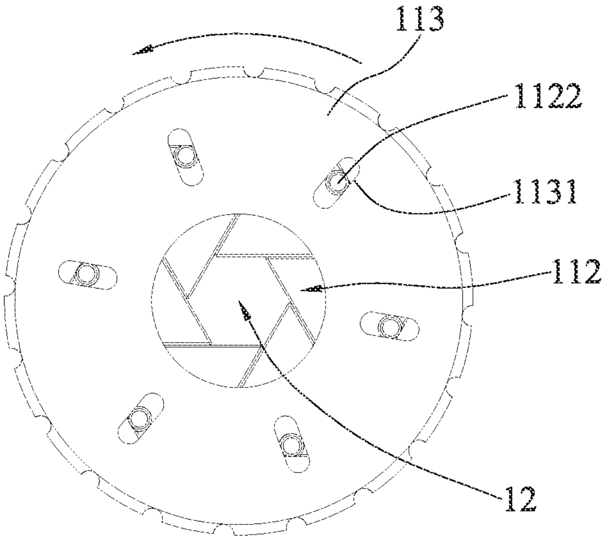
FIGS. 6A and 6B are schematic diagrams illustrating the adjustment gate of FIG. 4 during a rotation state.
Figure 6B:
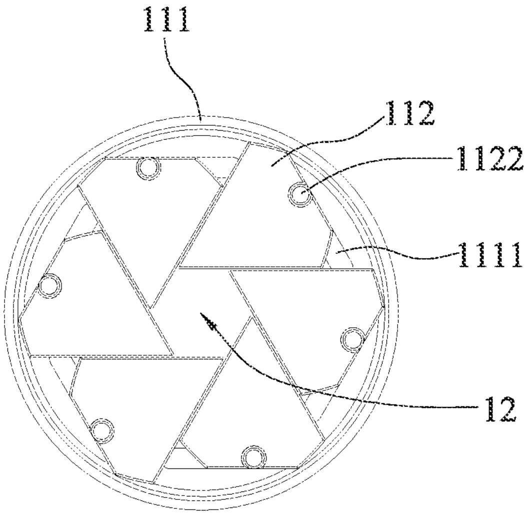

FIGS. 6A and 6B illustrate a state observed from the direction of arrow E shown in FIG. 4, where the rotation part 113 is in its rotation state that allows the aperture 12 to open towards its maximum diameter. For example, FIG. 6A shows that the pillars 1122 of the blades 112 are respectively moved toward one ends of the sliding slots 1131 (along their long axial direction) that are away from the center of the aperture 12, while FIG. 6B shows that with the blades 112 gradually opening the aperture 12, one ends of the sliding slots 1111 that are closest to the center of the aperture 12 are exposed by the blades 112, indicating that the pillars 1121 have been respectively moved to another ends of the sliding slots 1111 (along their long axial direction) that are away from the center of the aperture 12.

It should be noted that although there are six blades 112 shown in the embodiments of the adjustment gate 11, the number of the blades 112 (conjointly the number of the sliding slots 1111 and 1131) may configured to be more than six or less to one on demands, of which the present disclosure is not limited thereto.

It should also be noted that although the blades 112 shown in the embodiments of the adjustment gate 11 are in shapes of a triangle, the shape of the blades 112 may be polygonal, curved, irregular, or a complete or any partial portion of the combination of the above, of which the present disclosure is not limited thereto. For example, the blades 112 may have the shape of, including but not limited to, triangle, rectangle, rhombus, trapezoid, parallelogram, circle, ellipse, oval, ring, or a complete or any partial portion of the combination of the above.

It should further be noted that, the arrangements of the sliding slots 1111 and 1131 in the embodiments of the adjustment gate 11 are not limited to straight lines in polygon/radial arrangement, but can be designed in any suitable configuration for desired user experience in adjustment for the aperture 12. For example, the sliding slots 1111 and 1131 may be designed to allow discontinuous stepping adjustment for the aperture 12. In some embodiments, the sliding slots 1111 and 1131 may be designed in shapes of curved lines that allow smooth and gradual continuous adjustment. However, the present disclosure is not limited to those examples as discussed and may have other configurations.

Figure 7A:
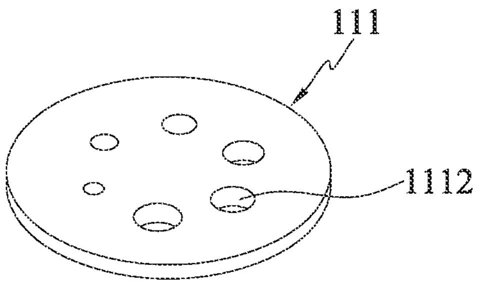
FIGS. 7A and 7B are schematic diagrams illustrating an embodiment of the structure of an adjustment gate in accordance with the present disclosure.
Figure 7B:
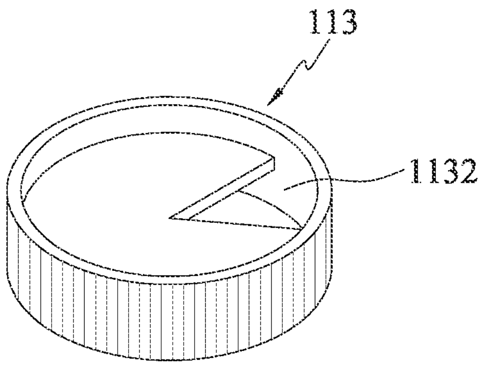

Referring to FIGS. 7A and 7B, an adjustment gate 11 of the present disclosure is further disclosed. In at least one embodiment, the adjustment gate 11 comprises a baffle 111 (referring to FIG. 7A) having a plurality of perforations 1112 with different sizes, and a rotation part 113 (referring to FIG. 7B) covering the baffle 111 and having a through hole 1132 formed thereon. In this configuration, the rotation part 113 is configured to rotate with respect to the baffle 111 fixed inside the flow channel 10F, thereby enabling the through hole 1132 to expose at least one of the perforations 1112 with different sizes to form the aperture 12 (i.e., the aperture 12 has an adjustable size). Accordingly, resistance in the flow channel 10F will be determined by perforations 1112 with different sizes exposed by the through hole 1132 for the patient to achieve optimal respiratory training efficiency.

It should be noted that although there are six perforations 1112 and one through hole 1132 shown in the embodiment of the adjustment gate 11, the number of the perforations 1112 and the through hole 1132 may vary on demands, of which the present disclosure is not limited thereto. Further, the sizes of each of the perforations 1112 and the through hole 1132 may also vary on demands. In at least one embodiment, the baffle 111 may be configured with a large amount of randomly arranged perforations 1112 with the same size, while the through hole 1132 may be configured to expose a determined amount of the perforations 1112 (which forms the aperture 12), so as to provide desired resistance in the flow channel 10F. In some embodiments, the through hole 1132 may be configured to expose more than one and/or partial of any of the perforations 1112 (which forms the aperture 12), so as to provide desired resistance in the flow channel 10F in a more precise measure. However, the scope of present disclosure is also not meant to be limited by the examples discussed, and variations are therefore can be exhaustive.

Figure 8:
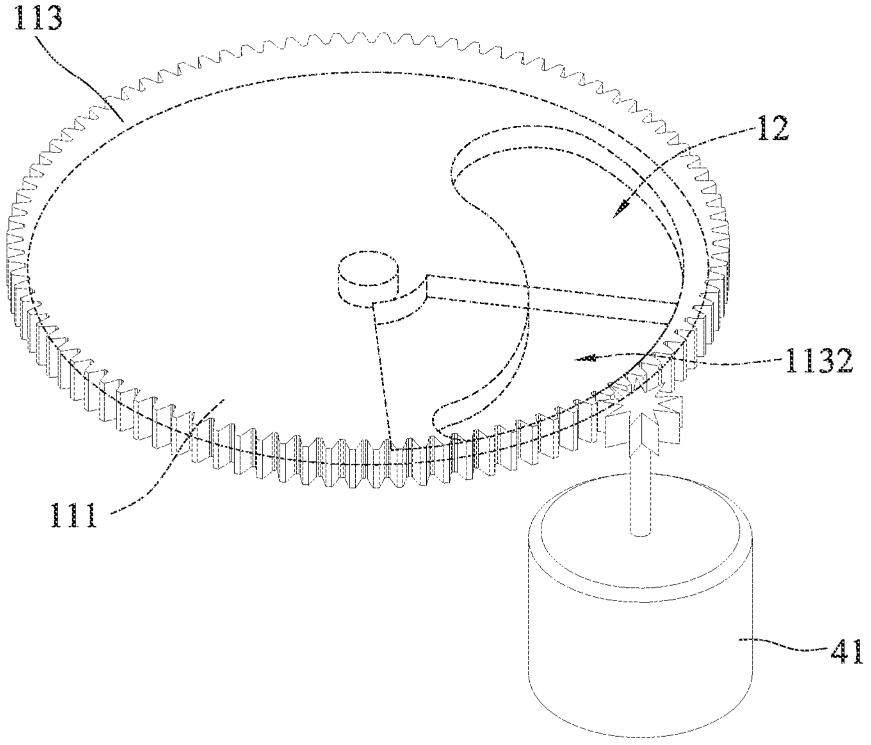
FIG. 8 is a schematic diagram illustrating an embodiment of the structure of an adjustment gate in accordance with the present disclosure.
Figure 9:
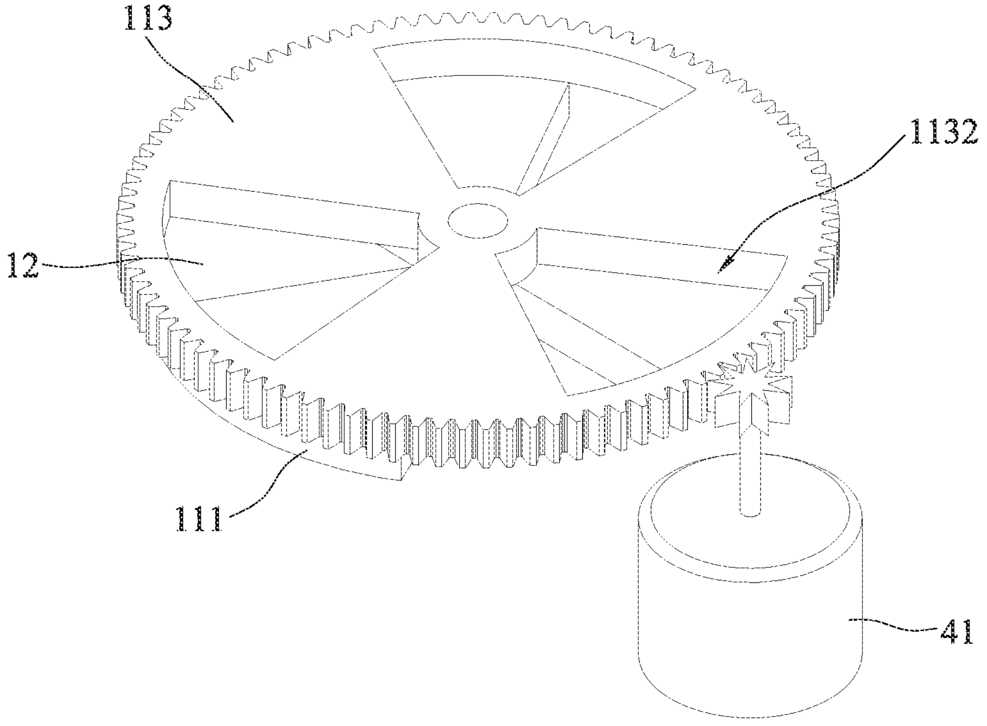
FIG. 9 is a schematic diagram illustrating an embodiment of the structure of an adjustment gate in accordance with the present disclosure.

In some embodiments, the adjustment gate 11 may be configured to adjust the size of the aperture 12 via manual or automatic means. FIGS. 8 and 9 show the examples of how the adjustment gate 11 performs said adjustment via automatic fashion.

Referring to FIG. 8, an adjustment gate 11 of the present disclosure is disclosed. In at least one embodiment, the adjustment gate 11 comprises a baffle 111 having an aperture 12 that expands gradually in size, and a rotation part 113 covering the baffle 111 and having a through hole 1132 formed thereon. Further, the processing module 40 is coupled to the rotation part 113 via a motor 41, whereas the motor 41 and the rotation part 113 are designed in a fitting gear arrangement, such that the motor 41 may drive (in response to an adjustment instruction produced by the processing module 40) the rotation part 113 to rotate the through hole 132 to expose a determined area of the aperture 12 to provide desired resistance in the flow channel 10F.

It should be noted that although the shape of the aperture 12 shown in the embodiments of the adjustment gate 11 takes up approximately half the area of the baffle 111, the aperture 12 may take up any desired area of the baffle 111 based on design requirements, of which the present disclosure is not limited thereto.

Referring to FIG. 9, an adjustment gate 11 of the present disclosure is disclosed. In at least one embodiment, the adjustment gate 11 comprises a baffle 111 having three radially arranged apertures 12 in shape of a sector with the same size, and a rotation part 113 covering the baffle 111 and having three radially arranged through holes 1132 corresponding in shape and size to the three apertures 12. Further, the processing module 40 is coupled to the rotation part 113 via a motor 41, whereas the motor 41 and the rotation part 113 are designed in a fitting gear arrangement, such that the motor 41 may drive (in response to an adjustment instruction produced by the processing module 40) the rotation part 113 to rotate the through holes 1132 to expose a determined area of the apertures 12 to provide desired resistance in the flow channel 10F.

It should be noted that although three apertures 12 and through holes 1132 are shown in the embodiments of the adjustment gate 11, there may be more or less number of apertures 12 and through holes 1132 configured in the adjustment gate 11, of which the present disclosure is not limited thereto. In addition, each of the apertures 12 and through holes 1132 may also differ in shape, size and number on demands, as long as variance in the resistance in the flow channel 10F may be achieved via rotation of the rotation part 113, of which the present disclosure is also not limited thereto.

It should be further noted that FIGS. 8 and 9 are only exemplary illustrations of how automatic adjustment of the adjustment gate 11 is achieved. However, the automatic adjustment of the adjustment gate 11 in this disclosure is not meant to be limited by said embodiments of the adjustment gate 11. For example, as long as gear arrangement between the rotation part 113 and the motor 41 is achieved, the adjustment gate 11 may be implemented as any one of the aforementioned embodiments in automatic fashion. Moreover, the gear arrangement between the motor 41 and the rotation part 113 is not limited to an outer ring of the rotation part 113 and may be arranged at any part of the rotation part 113, such as the rotation axis of the rotation part 113. Furthermore, the motor 41 is not limited to physically coupled with the processing module 40 and can be activated by the processing module 40 via wireless communication through the wireless transmission module 70.

No matter which embodiment of the adjustment gate 11 is utilized for the respiratory adjustment unit 10, the adjustment gate 11 is to adjust the size of the aperture 12 and provide determined resistance in the flow channel 10F during respiratory training. For example, the aperture 12 may have a minimum diameter of any one of 0.01 mm, 0.05 mm, 0.1 mm, 0.5 mm, 1 mm, 1.5 mm, 2 mm, 2.5 mm, 3 mm, 3.5 mm or 4 mm, and the aperture 12 may have a maximum diameter of any one of 10 mm, 9.5 mm, 9 mm, 8.5 mm, 8 mm, 7.5 mm, 7 mm, 6.5 mm, 6 mm, 5.5 mm, 5 mm, or 4.5 mm, of which the present disclosure is not limited thereto. In some embodiments, the aperture 12 may have an adjustable diameter range between 0.01 mm to 10 mm, 3 mm to 11 mm or 3 mm to 5 mm, of which the present disclosure is also not limited thereto. In some embodiments, the aperture 12 with the diameter of 3 mm provides resistance of about 40.3 mmHg in the flow channel 10F; the aperture 12 with the diameter of 5 mm provides resistance of about 35.9 mmHg in the flow channel 10F; the aperture 12 with the diameter of 7.5 mm provides resistance of about 29.1 mmHg in the flow channel 10F; the aperture 12 with the diameter of 9 mm provides resistance of about 25.4 mmHg in the flow channel 10F; and the aperture 12 with the diameter of 11 mm provides resistance of about 17 mmHg in the flow channel 10F, but it is noted that said relationship between the size of the aperture 12 and the resistance in the flow channel 10F may still vary depending on the structural design of the device 1, which is also not restrictive of the scope of the present disclosure.

Figure 10:
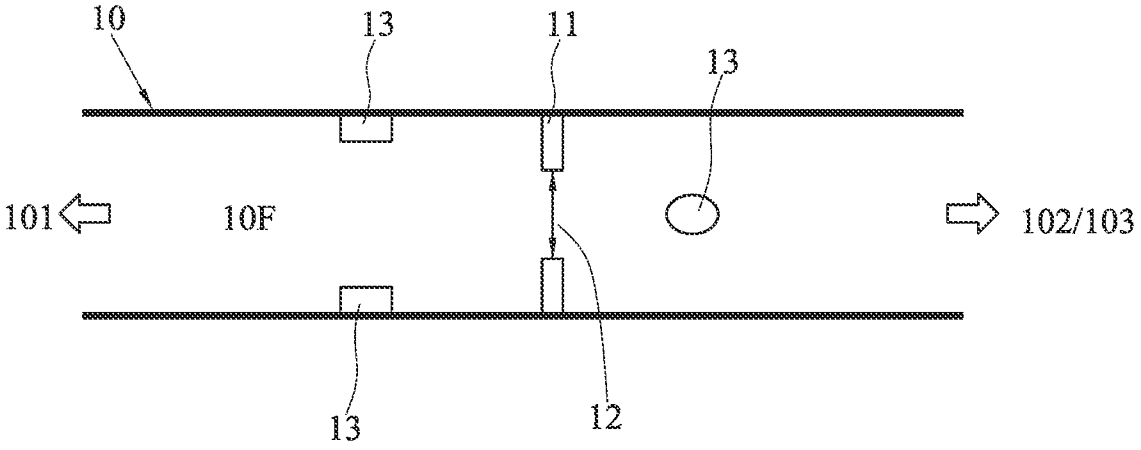
FIG. 10 is a schematic diagram illustrating configurations of pressure sensors in accordance with the present disclosure.

Referring to FIG. 10, the arrangement of the pressure sensors 13 is further explained. For example, pressure sensors 13 may be arranged on the inner wall of the flow channel 10F about the adjustment gate 11 (i.e., a distance between the pressure sensors 13 and the adjustment gate 11 is shorter than a distance between the pressure sensors 13 and the first opening end 101/second opening end 102/third opening end 103) to detect the positive pressure derived from resistance in the flow channel 10F generated by exhale/inhale forces of the patient. In some embodiments, considering the scenario where the patient is performing respiratory training using the device 1 (the first opening end 101 is facing the patient), two pressure sensors 13 are oppositely disposed on the left and right sidewalls of the flow channel 10F at the front side of the adjustment gate 11, while a third pressure sensor 13 is disposed on the top of the inner wall of the flow channel 10F at the back side of the adjustment gate 11. In such configuration, the pressure signal (denoted as P1) from the front-left pressure sensor 13 and the pressure signal (denoted as P3) from the back-top pressure sensor 13 may be used to estimate functionality of the patient's right lung, and the pressure signal (denoted as P2) from the front-right pressure sensor 13 and the pressure signal (denoted as P3) from the back-top pressure sensor 13 may be used to estimate functionality of the patient's left lung, which may be expressed as the following expression:

$$\Delta P_A = P_1 - P_3 \quad (1) \text{ and}$$

$$\Delta P_B = P_2 - P_3 \quad (2),$$

where $\Delta P_A$ represents a pressure difference between the front and back sides of the adjustment gate 11 on the left side of the flow channel 10F, which may be derived as an amount of the air flow on the left side of the flow channel 10F, and thus may be used to indicate the functionality of the patient's right lung, and $\Delta P_B$ represents a pressure difference between the front and back of the adjustment gate 11 on the right side of the flow channel 10F, which may be derived as an amount of the air flow on the right side of the flow channel 10F, and thus may be used to indicate the functionality of the patient's left lung.

Based on the above, the pressure differences $\Delta P_A$ and $\Delta P_B$, due to resistance caused by the adjustment gate 11, may be used to derive airflow volume (e.g., with application of Bernoulli's principle), and be useful in monitoring the inhale/exhale force and duration of the patient during respiratory training.

Additionally, the pressure differences $\Delta P_A$ and $\Delta P_B$ may be utilized to estimate entropy of lung airflow of the patient, which is useful to determine if respiratory tracts of the patient have one-sided abnormality or having sputum stocked therein. The entropy of lung airflow of the patient may be expressed as follows:

$$\text{Entropy} = \sqrt{\Delta\Delta P_A^2 + \Delta P_B^2 - 2\Delta P_A \Delta P_B} \quad (3).$$

In general, the larger the entropy, the more likely abnormalities are present within respiratory tracts or lung of the patient. Therefore, the calculation of entropy is useful for detecting deterioration of respiratory tracts at an early stage.

It should be noted that the pressure differences $\Delta P_A$ and $\Delta P_B$ may have other applications. For example, said pressure differences $\Delta P_A$ and $\Delta P_B$ may be further utilized to calculate an airflow rate, respiratory frequency, or even dosage taken of the patient during respiratory training. In some embodiments, said pressure differences $\Delta P_A$ and $\Delta P_B$ may be processed with other signals (e.g., a cardiovascular signal) derived from respiratory training of the patient to determine other conditions of the patient during respiratory training.

It should be further noted that the configuration of pressure sensors 13 are not limited to those described above. For example, for a pressure sensor 13 with enough sensitivity to distinguish the pressure differences $\Delta P_A$ and $\Delta P_B$, the number of pressure sensors 13 may be reduced to less than three. Further, there may be more than three pressure sensors 13 disposed about the adjustment gate 11, so as to detect more details regarding the patient's respiratory performances. Nevertheless, without straying from the concept of the calculation above, the scope of the present disclosure is not meant to be limited by the arrangement of the pressure sensors 13.

In at least one embodiment, the processing module 40 of the present disclosure is configured to perform the above calculation upon receiving the pressure signals from the pressure sensors 13. The processing module 40 may receive said pressure signals via either wired (e.g., the pressure sensors 13 are connected to the processing module 40) or wireless (e.g., pressure signals are transmitted by the wireless transmission module 70) communication. Further, after said calculation, the processing module 40 may further produce an adjustment instruction to instruct (e.g., via the indicating device 60) the patient (or the user) to manually adjust the adjustment gate 11 or instruct the motor 41 (if present) to automatically adjust the adjustment gate 11, based on an indication that the current resistant in the flow channel 10F is too high or too low for the patient.

Figure 11:
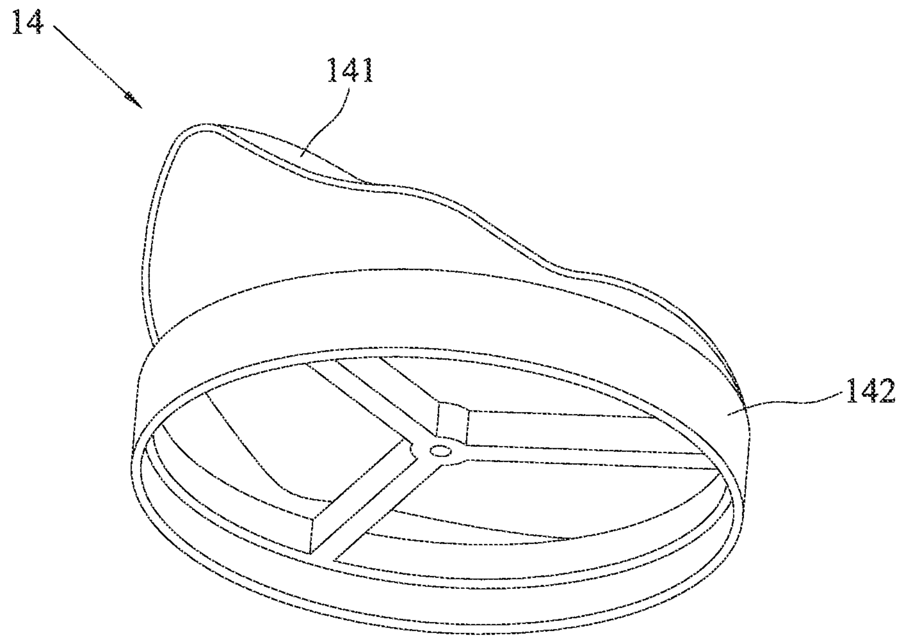
FIG. 11 is a schematic diagram illustrating the structure of a check valve in accordance with the present disclosure.

Referring to FIG. 11, the configuration of the check valve 14 is disclosed. In at least one embodiment, the check valve 14 of the present disclosure comprises a film cap 141 of any soft and elastic materials (e.g., silicone) and a support structure 142 that holds the film cap 141. For example, the film cap 141 is partially attached to the support structure 142, and the support structure 142 is fixed in place inside the flow channel 10F. In such configuration, the check valve 14 can keep passage in the flow channel 10F unblocked when airflow in the flow channel 10F is absent or is passing in a desired direction (e.g., air will push the film cap 141 away from the support structure 142). On the other hand, when airflow in the flow channel 10F is passing in an undesired direction, the film cap 141 will close up the passage in the flow channel 10F, thereby enabling the air flow into other regions in the device 1 (e.g., flowing to another flow channel or returning to the mouthpiece 80).

When referring back to the embodiments of the device 1 as shown in FIGS. 2, 3A and 3B, one of ordinary skill in the art would understand how the check valve 14 operates during exhale and inhale of the patient. Taking the embodiment of the device 1 shown in FIG. 2 as an example, the check valve 14 would allow air flow from the second opening end 102 toward the first opening end 101 during inhale (see arrows A) but block air flow from the first opening end 101 toward the second opening end 102, thereby enabling the airflow to directly enter into the vibration generating unit 30 during exhale (see arrows B). Further, taking the embodiment of the device 1 shown in FIG. 3B as another example, the check valve 14 in the exhaling route (referring to the arrow C) will prevent air flow from the second opening end 102 toward the first opening end 101, whereas the check valve 14 in the inhaling route (referring to the arrow D) will prevent air flow from the first opening end 101 toward the third opening end 103, such that the single-direction inhaling route and the single-direction exhaling route may be clearly distinguished.

Figure 12:
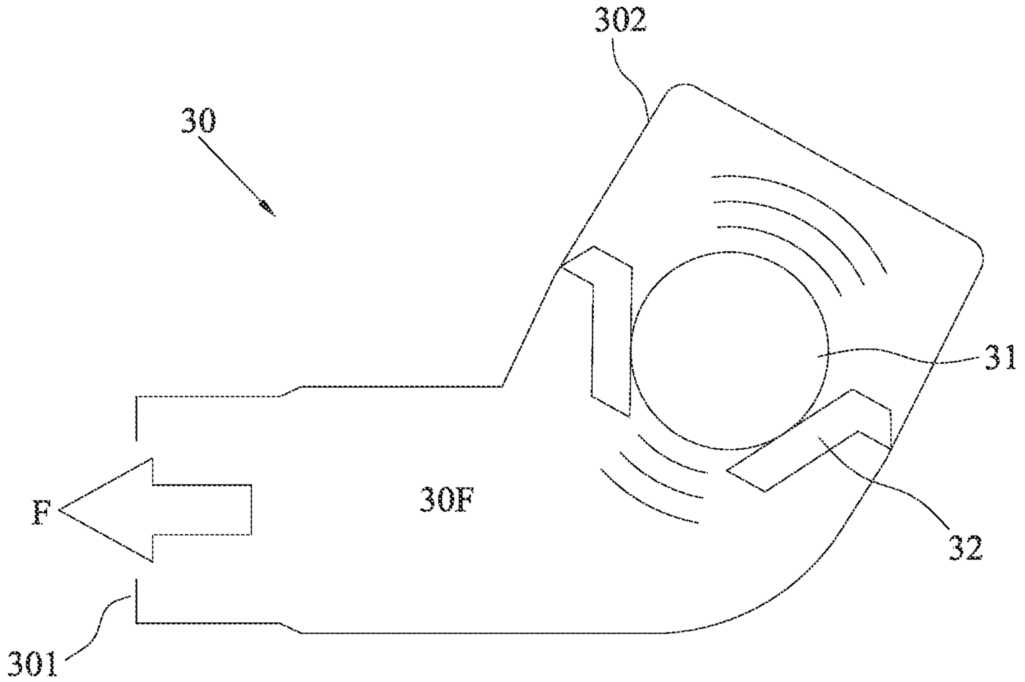
FIG. 12 is a schematic diagram illustrating an embodiment of the structure of a vibration generating unit in accordance with the present disclosure.
Figure 13:
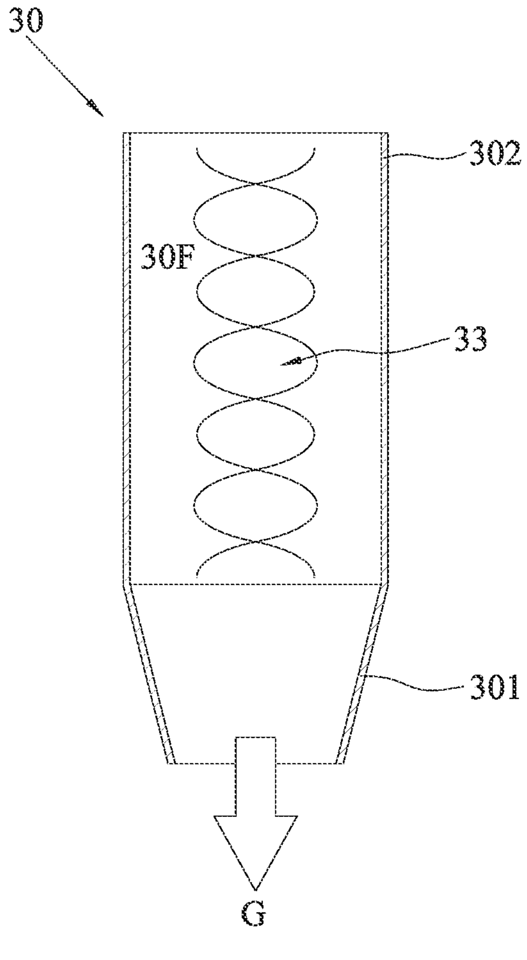
FIG. 13 is a schematic diagram illustrating an embodiment of the structure of a vibration generating unit in accordance with the present disclosure.
Figure 14:
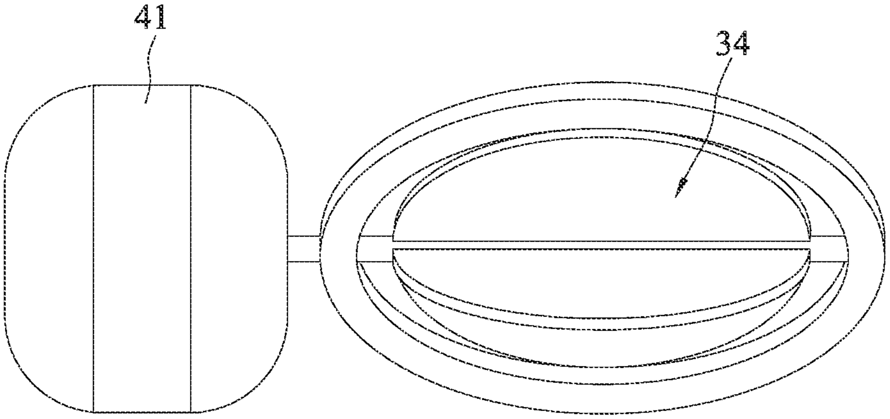
FIG. 14 is a schematic diagram illustrating an embodiment of the structure of a vibration generating unit in accordance with the present disclosure.

FIGS. 12 to 14 exemplify variations of the vibration generating unit 30 and its relationship with other components in the device 1 in accordance with embodiments of the present disclosure.

FIG. 12 shows an embodiment of the vibration generating unit 30 of the present disclosure. In at least one embodiment, the vibration generating unit 30 of the present disclosure comprises a fourth opening end 301 which is an insertion end (see arrow F) to the device 1 of any of the embodiments as discussed above, and a fifth opening end 302 in communication with the fourth opening end 301 to form a flow channel 30F. The vibration generating unit 30 further comprises a vibration element disposed in the flow channel 30F that induces vibration into said flow channel 30F and the flow channel 10F/10F-1/10F-2 connected thereto.

In some embodiments, the vibration element of the vibration generating unit 30 comprises a ball 31 (e.g., a steel ball) and a support 32 that loosely keeps the ball 31 in an upright direction (with respect to the gravity). In this configuration, airflow due to inhale/exhale of the patient will cause the ball 31 to vibrate and resonate the flow channels 30F and 10F/10F-1/10F-2, such that the vibration may assist the patient to cough out sputum during respiratory training.

The vibration generating unit 30 shown in FIG. 12 is illustrated under the consideration to be inserted into (or coupled with) the second opening end 102 of the device 1 of the present disclosure, where the fifth opening end 302 may be covered (e.g., having a lid disposed thereon) to prevent the ball 31 from falling out. However, it should be understood that this embodiment of the vibration generating unit 30 is also compatible for other embodiments of the device 1 of the present disclosure. For example, the vibration generating unit 30 may have its fourth opening end 301 coupled with the flow channel 10F of the device 1 with its fifth opening end 302 covered, while the support 32 is arranged upside down to loosely keep the ball 31 in an upright direction (with respect to the gravity). In some embodiments, as shown in FIGS. 3A and 3B, the vibration generating unit 30 may have its fourth opening end 301 coupled with the second opening end 102 or the third opening end 103 of the device 1, where vibration generated by the ball 31 may resonate the exhaling route or the inhaling route while the support 32 loosely keep the ball 31 in an upright direction (with respect to the gravity) substantially perpendicular to the direction of flow channels 10F-1 and 10F-2.

FIG. 13 shows another embodiment of the vibration generating unit 30 of the present disclosure. In at least one embodiment, the vibration generating unit 30 of the present disclosure comprises a fourth opening end 301 which is an insertion end (see arrow G) to the device 1 of any of the embodiments as discussed above, and a fifth opening end 302 in communication with the fourth opening end 301 to form a flow channel 30F. The vibration generating unit 30 further comprises a vibration element disposed in the flow channel 30F that induces vibration into said flow channel 30F and the flow channel 10F/10F-1/10F-2 connected thereto.

In some embodiments, as shown in FIG. 13, the vibration element of the vibration generating unit 30 comprises a spiral fan 33 extending in direction of the flow channel 30F. In this configuration, airflow due to inhale/exhale of the patient will rotate the spiral fan 33 to induce vibration and resonate the flow channel 30F and 10F/10F-1/10F-2, such that the vibration may assist the patient to cough out sputum during respiratory training.

The vibration generating unit 30 shown in FIG. 13 is illustrated under the consideration to be inserted into (or coupled with) the second opening end 102 or flow channel 10F of the embodiments of the device 1 of the present disclosure, where the fifth opening end 302 may be covered (e.g., having a lid disposed thereon) to prevent the spiral fan 33 from falling out. However, it should be understood that the vibration generating unit 30 of the present disclosure is also compatible for other embodiments of the device 1 of the present disclosure. For example, as shown in FIGS. 3A and 3B, the vibration generating unit 30 may have its fourth opening end 301 coupled with the second opening end 102 or the third opening end 103 of the device 1 of the present disclosure, where the vibration induced by the spiral fan 33 may resonate the exhaling route or the inhaling route during respiratory training.

In some embodiments, the vibration generating unit 30 may be configured to induce vibration via manual or automatic means. For example, vibration frequency of the vibration element would be adjustable in response to the vibrate capability thereof. In some embodiments, said vibration frequency may be manually affected by the amount of airflow applicable in the flow channel 30F (e.g., the size of the aperture 12 and/or the exhale/inhale force of the patient).

In some embodiments, said vibration frequency may also be set by automatically changing the vibrate capability of the vibration element. For example, FIG. 14 illustrates an example of how the vibration generating unit 30 induces vibration via an automatic fashion. In FIG. 14, only the vibration element within the flow channel 30F is illustrated, and configurations of the fourth opening end 301, fifth opening end 302 and flow channel 30F of the vibration generating unit 30 are omitted for the convenience of illustration. However, one of ordinary skill in the art should understand that the vibration generating unit 30 shown in FIG. 14 is also compatible for the device 1 of any of the embodiments as discussed above.

For example, as shown in FIG. 14, the vibration element of the present disclosure comprises a fan set 34 arranged like a waterwheel. Further, the processing module 40 is coupled to the fan set 34 via a motor 41, such that the motor 41 may rotate (in response to an adjustment instruction produced by the processing module 40) the fan set 34 to induce vibration in desired vibration frequency and resonate the flow channels 30F and 10F/10F-1/10F-2.

It should be noted that FIG. 14 is only an exemplary illustration of how automatic vibration generation of the vibration generating unit 30 is achieved. However, the automatic vibration generation of the vibration generating unit 30 in this disclosure is not meant to be limited by said embodiment of the vibration generating unit 30 of the present disclosure. For example, as long as the motor 41 is set to drive the vibration element to induce vibration (e.g., the motor 41 may be configured to cause the ball 31 to vibrate or the spiral fan 33 to rotate), the vibration generating unit 30 may be implemented as any one of the aforementioned embodiments in an automatic manner. Moreover, the motor 41 is not limited to physically coupled with the processing module 40 and can be activated by the processing module 40 via wireless communication through the wireless transmission module 70.

In some embodiments, a vibration sensor (not shown) may also be disposed within the flow channel 30F of the vibration generating unit 30, so as to detect vibration signals regarding the vibration elements. Said vibration sensor may be any one of piezoresistive sensor, piezoelectric sensor, capacitive sensor, optical fiber sensor, accelerometer, Linear Variable Differential Transformer (LVDT) or the like. Said vibration signal may be sent (in a wired or wireless manner) to the processing module 40 to determine whether the vibration frequency is too high or too low for the patient. For example, depending on whether the vibration frequency is too high or too low, the processing module 40 may produce an adjustment instruction for the indicating device 60 or the motors 41, such that the aperture 12 of the adjustment gate 11 and/or the vibration frequency of the vibration element may be correspondingly adjusted (manually or automatically).

Figure 15:
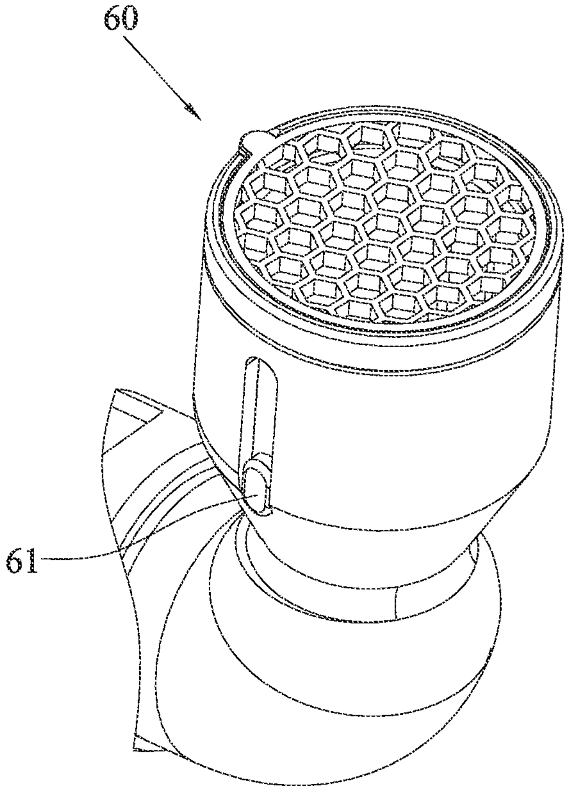
FIG. 15 is a schematic diagram illustrating an embodiment of an indicating device in accordance with the present disclosure.
Figure 16:
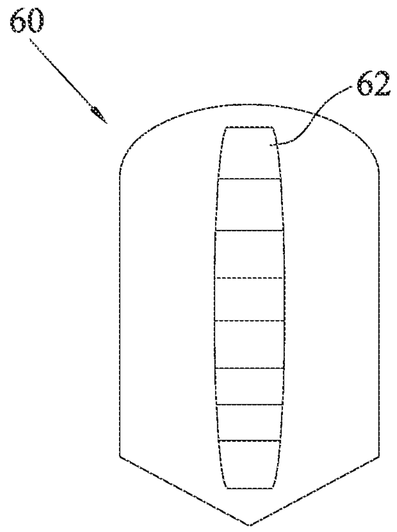
FIG. 16 is a schematic diagram illustrating an embodiment of an indicating device in accordance with the present disclosure.
Figure 17:
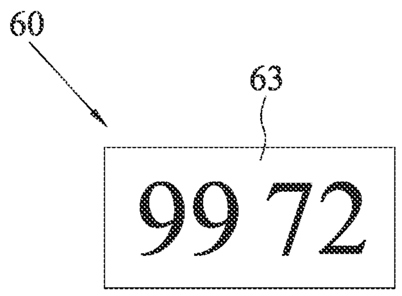
FIG. 17 is a schematic diagram illustrating an embodiment of an indicating device in accordance with the present disclosure.

FIGS. 15 to 17 exemplify variations of the indicating device 60 and its relationship with other components in the device 1 in accordance with embodiments of the present disclosure.

FIG. 15 shows an embodiment of the indicating device 60 of the present disclosure. In at least one embodiment, the indicating device 60 comprises an indicating element 61 having a sliding bar with various color blocks and an indicating knot that slides on the sliding bar. For example, the indicating element 61 may be installed to the outer wall of any types of the respiratory adjustment unit 10 of the device 1 as discussed above. As the patient is exhaling/inhaling through the device 1, the indicating knot may slide on the sliding bar in response to force of airflow and visually present color blocks that indicate the respiratory performance of the patient (e.g., poor or unsatisfied force output may result in red and/or yellow blocks on the sliding bar to be revealed by the indicating knot, while adequate force output may result in green blocks on the sliding bar to be revealed by the indicating knot).

FIG. 16 shows an embodiment of the indicating device 60 of the present disclosure. In at least one embodiment, the indicating device 60 of the present disclosure comprises a light set 62 having a plurality of lights, where each of the plurality of lights may be configured to emit the same or different colored lights. For example, the light set 62 may be installed to the outer wall of any types of the respiratory adjustment unit 10 of the device 1 as discussed above, and various lighting patterns of the light set 62 may be utilized to visually indicate the respiratory performance of the patient.

In some embodiments, the light set 62 may be piezoelectric sensitive, which lights up partial or all of the plurality of lights in response to force of airflow during respiratory training of the patient. In some embodiments, the light set 62 may be coupled with the processing module 40 via wired or wireless communication, such that the light set 62 may light up partial or all of the plurality of lights in response to an adjusting instruction produced by the processing module 40 regarding signals derived from the device 1 with respect to the respiratory training of the patient. In some embodiments, the lighting pattern of the light set 62 may utilize red light to indicate poor force output, yellow light to indicate unsatisfied force output, and green light to indicate adequate force output. In some embodiments, the lighting pattern of the light set 62 may utilize a ratio of on/off lights to indicate the respiratory performance of the patient. However, other configurations for the light set 62 may also be utilized, of which the present disclosure is not limited thereto.

FIG. 17 shows an embodiment of the indicating device 60 of the present disclosure. In at least one embodiment, the indicating device 60 of the present disclosure comprises a display 63 that presents the respiratory performance of the patient in texts. For example, the display 63 may be installed to the outer wall of any types of the respiratory adjustment unit 10 of the device 1 as discussed above, and the display 63 may be coupled to the processing module 40 via wired or wireless communication. As the patient is exhaling/inhaling through the device 1, signals regarding respiratory training of the patient derived and processed by the processing module 40 may be presented on the display 63 in text form, where the text may be, but not limited to, pressure values corresponding to pressure signals, vibration frequencies corresponding to vibration signals, blood pressure corresponding to cardiovascular signals, etc.

It should be noted that the scope of the present disclosure is not meant be limited by the embodiments of the indicating device 60 described above, and the indicating device 60 may be configured in other forms based on design requirements. For example, the indicating device 60 may indicate the respiratory performance of the patient via sound, vibration, lighting frequency, lighting brightness/darkness degree, etc., of which the present disclosure is not limited thereto. In an embodiment, the indicating device 60 may instead realize as an interactive application installed in mobile devices, such that signals regarding respiratory training of the patient derived and processed by the processing module 40 may be presented to the patient (or user) via animation, drawings, lists, diagrams, charts, voice service, or any interactive forms, of which the present disclosure is also not limited thereto.

In summary, for various types of embodiments, the device for pulmonary rehabilitation of this disclosure is configured to provide adjustable resistance for the patient during respiratory training on demands so as to improve rehabilitation efficiency. Moreover, said device is configured to adapt a variety of external parts to assist on medication dosing, information processing, and/or sputum removal for the patient during respiratory training. Therefore, optimal efficiency for pulmonary rehabilitation and smooth experience during respiratory training for the patient is achieved.

The present disclosure has been described with exemplary embodiments to illustrate the features, and efficacies of the present disclosure, but not intended to limit the implementation scope of the present disclosure. The present disclosure without departing from the scope of the premise can make various changes and modifications by a person skilled in the art. However, any equivalent change and modification accomplished according to the disclosure of the present disclosure should be considered as being covered in the scope of the present disclosure. The scope of the disclosure should be defined by the appended claims.

What is claimed is:

1. A device for pulmonary rehabilitation, comprising:

a mouthpiece; and a respiratory adjustment unit detachably connected to the mouthpiece and having a first opening end and a second opening end in communication to each other to form a first flow channel, wherein the respiratory adjustment unit further comprises a first adjustment gate disposed in the first flow channel, and the first adjustment gate includes:

a first baffle having a first aperture with an adjustable size; and a first blade configured to slide on the first baffle to partially or completely cover the first aperture, wherein the first baffle has a first sliding slot, and the first blade has a first surface with a first pillar and a second surface opposed to the first surface, and wherein the first pillar is disposed in the first sliding slot and configured to reciprocate along a long axial direction of the first sliding slot.

2. The device of claim 1, wherein the respiratory adjustment unit has a third opening end in communication with the first opening end to form a second flow channel, and the respiratory adjustment unit further comprises a second adjustment gate disposed in the second flow channel and including a second baffle having a second aperture with an adjustable size.

3. The device of claim 2, wherein the second adjustment gate further comprises a second blade configured to slide on the second baffle to partially or completely cover the second aperture.

4. The device of claim 3, wherein:

the second baffle has a third sliding slot, and the second blade has a third surface with a third pillar and a fourth surface opposed to the third surface, wherein the third pillar is disposed in the third sliding slot and configured to reciprocate along a long axial direction of the third sliding slot.

5. The device of claim 4, wherein:

the first adjustment gate further comprises a first rotation part having a second sliding slot, the second surface of the first blade has a second pillar disposed in the second sliding slot and configured to reciprocate along a long axial direction of the second sliding slot, and the first rotation part is configured to drive the first pillar and the second pillar to reciprocate within the first sliding slot and the second sliding slot respectively during a rotation state of the first rotation part to enable the first blade to slide on the first baffle; and the second adjustment gate further comprises a second rotation part having a fourth sliding slot, the fourth surface of the second blade has a fourth pillar disposed in the fourth sliding slot and configured to reciprocate along a long axial direction of the fourth sliding slot, and the second rotation part is configured to drive the third pillar and the fourth pillar to reciprocate within the third sliding slot and the fourth sliding slot respectively during a rotation state of the second rotation part to enable the second blade to slide on the second baffle.

6. The device of claim 2, wherein:

the first adjustment gate further comprises a first rotation part having a first through hole formed thereon and covering the first baffle having a plurality of first perforations with different sizes, wherein the first rotation part is configured to rotate with respect to the first baffle to enable the first through hole to expose at least one of the plurality of first perforations with different sizes to form the first aperture; and/or the second adjustment gate further comprises a second rotation part having a second through hole formed thereon and covering the second baffle having a plurality of second perforations with different sizes, wherein the second rotation part is configured to rotate with respect to the second baffle to enable the second through hole to expose at least one of the plurality of second perforations with different sizes to form the second aperture.

7. The device of claim 2, further comprising:

a first pressure sensor and a second pressure sensor, wherein the first pressure sensor is disposed in the first flow channel at one side of the first adjustment gate to measure a first pressure signal, and the second pressure sensor is disposed in the first flow channel at the other side of the first adjustment gate to measure a second pressure signal; and/or a third pressure sensor and a further pressure sensor, wherein the third pressure sensor is disposed in the second flow channel at one side of the second adjustment gate to measure a third pressure signal, and the fourth pressure sensor is disposed in the second flow channel at the other side of the second adjustment gate to measure a fourth pressure signal.

8. The device of claim 7, further comprising a processing module coupled with the first pressure sensor and the second pressure sensor to receive and process the first pressure signal and the second pressure signal, and/or coupled with the third pressure sensor and the fourth pressure sensor to receive and process the third pressure signal and the fourth pressure signal.

9. The device of claim 8, further comprising an indicating device coupled with the processing module and configured to send indication information to a user based on an adjustment instruction from the processing module.

10. The device of claim 9, wherein:

the adjustment instruction is generated according to the first pressure signal, the second pressure signal, the third pressure signal, the fourth pressure signal, and any combination thereof, provided that the processing module receives and processes the first pressure signal, the second pressure signal, the third pressure signal, the fourth pressure signal, and any combination thereof.

11. The device of claim 9, further comprising a wireless transmission module coupled with the processing module and configured to receive and send an outputting signal to the processing module to generate the adjustment instruction and/or to send a signal received and processed by the processing module for outputting.

12. The device of claim 8, wherein:

the processing module is coupled with the first adjustment gate to send an adjustment instruction to the first adjustment gate, and the first adjustment gate is configured to adjust the size of the first aperture based on the adjustment instruction; and/or the processing module is coupled with the second adjustment gate to send the adjustment instruction to the second adjustment gate, and the second adjustment gate is configured to adjust the size of the second aperture based on the adjustment instruction.

13. The device of claim 7, wherein a distance between the first pressure sensor and the first adjustment gate is shorter than a distance between the first pressure sensor and the first opening end, and wherein a distance between the third pressure sensor and the second adjustment gate is shorter than a distance between the third pressure sensor and the first opening end.

14. The device of claim 7, further comprising a fifth pressure sensor disposed in the first flow channel to measure a fifth pressure signal, and/or a sixth pressure sensor disposed in the second flow channel to measure a sixth pressure signal.

15. The device of claim 2, further comprising:

a first check valve disposed in the first flow channel to block airflow flowing from the second opening end to the first opening end; and/or a second check valve disposed in the second flow channel to block the airflow flowing from the third opening end to the first opening end.

16. The device of claim 2, further comprising a dosing unit coupled with the second opening end or the third opening end to provide medication into the first flow channel and the second flow channel, respectively.

17. The device of claim 2, further comprising a vibration generating unit coupled with at least one of the second opening end and the third opening end to induce vibration and resonate the first flow channel and/or the second flow channel.

18. The device of claim 17, further comprising a processing module coupled with the vibration generating unit, wherein the vibration generating unit comprises a vibration sensor configured to measure a vibration signal, and the processing module is configured to receive and process the vibration signal.

19. The device of claim 17, wherein the vibration generating unit has a fourth opening end in communication with a fifth opening end to form a third flow channel, and the vibration generating unit further comprises a vibration element disposed within the third flow channel, and wherein the fourth opening end is detachably coupled with the second opening end or the third opening end.

20. The device of claim 2, further comprising:

a cardiovascular sensor coupled with the respiratory adjustment unit and configured to measure a cardiovascular signal; and a processing module coupled with the cardiovascular sensor to receive and process the cardiovascular signal.

* * * * *